(12) United States Patent  (10) Patent No.: US 6,352,505 B1
Bortz  (45) Date of Patent: Mar. 5, 2002

(54) DEVICE FOR DIABETES MANAGEMENT

(76) Inventor: Jonathan David Bortz, 6520 Clayton Rd., St. Louis, MO (US) 63117

( * ) Notice: Subject to any disclaimer, the term of this patent is extended or adjusted under 35 U.S.C. 154(b) by 0 days.

(21) Appl. No.: 09/415,361

(22) Filed: Oct. 8, 1999

Related U.S. Application Data

(63) Continuation of application No. 08/912,740, filed on Aug. 18, 1997, now Pat. No. 5,997,475.

(51) Int. Cl.$^7$ .................................................. A61B 5/00
(52) U.S. Cl. ......................... 600/300; 600/365; 702/19; 128/920
(58) Field of Search ................................ 600/300, 365; 128/921, 920; 708/100, 131, 133, 142, 160; 702/19

(56) References Cited

U.S. PATENT DOCUMENTS 4,731,726 A * 3/1988 Allen, III
5,691,927 A * 11/1997 Gump
5,822,715 A * 10/1998 Worthington et al. ......... 702/19

* cited by examiner

Primary Examiner—Roy Gibson
(74) Attorney, Agent, or Firm—Haverstock, Garrett & Roberts LLP

(57) ABSTRACT

A device for management of diabetes is disclosed which comprises a programmable microprocessor based unit having a display, keyboard, and memory, the keyboard for inputting information concerning carbohydrates ingested by a user, the microprocessor being programmed to determine an amount of insulin to be used by a user based upon the carbohydrates ingested and the display displaying the amount of insulin to be used.

16 Claims, 3 Drawing Sheets

DEVICE FOR DIABETES MANAGEMENT

This application is a continuation of Ser. No. 08/912,740 Aug. 18, 1997 U.S. Pat. No. 5,997,475 issued Dec. 7, 1999.

BACKGROUND OF THE INVENTION

This invention relates to a device for diabetes management and more particularly to a hand-held electronic device for determining a proper insulin dosage based upon the content of carbohydrates in foods ingested by a user.

Control of certain health conditions typically involves the frequent monitoring of the health of a person. In order to monitor the health conditions the person is required to participate at a high and consistent level. One health condition which needs to be monitored is diabetes. For the care of diabetes it has been important to monitor the blood glucose level of the individual and to somehow record the level along with the date and time of the monitoring. Additionally, it is useful to be able to track diet, exercise, and medication of the diabetic in order to correctly and effectively determine if any change to the diabetic's therapy will be needed.

There have been some electronic devices which have been proposed and used in the past to monitor blood glucose which were inexpensive and easy to use. However, such devices are only able to monitor the blood glucose level and cannot monitor other conditions such as diet or exercise. Additionally, there have been developed microprocessor based blood glucose monitoring systems. However, such systems have several disadvantages. For example, such microprocessor based systems have only limited capability in being able to monitor what kind of meal was eaten prior to the blood glucose reading being taken.

In the management of diabetes it has been found that it is advantageous to monitor a patient's eating and exercise to determine the optimum insulin dosage required for that patient. With respect to monitoring a patient's eating it is extremely important to monitor the amount of carbohydrates which plays a critical role in determining the blood glucose level. Research has confirmed that if diabetic patients can control their blood glucose levels effectively they will reduce risk in developing many of the health complications well known in diabetes.

Controlling the diet is the cornerstone of diabetes management and in recent years greater attention has been focused on meals and the amount of carbohydrates consumed. This is because it has been recognized that the amount of carbohydrates consumed in a diet is the single largest contributor to the body's glucose level after a meal. The only method known to record such information has been by writing it down in a log book. Additionally, the recording of such information is very subjective and requires the user to guess at various amounts of carbohydrates actually eaten. Due to the subjective nature of this method, the proper insulin dosage may not be calculated accurately.

The present invention is designed to provide a diabetic patient with a reliable and accurate tool to measure the amount of carbohydrates prior to consumption of a meal. With such information the diabetic patient is able to calculate an appropriate insulin dose to administer prior to a meal. The present invention further serves as an educational tool to make a patient aware of the importance of carbohydrates consumed. The patient, with continued use of the device of the present invention, may be trained to evaluate carbohydrate content of foods so that the patient will in time have the ability to better understand dosage requirements based on diet. Additionally, health care professionals will be better able to assist their patients in complying with the patient's prescribed guidelines for diet management if the amount of carbohydrates consumed by the patient is known. The device also provides a record whereby diet and other components of care can be evaluated and modified by the health care professional as needed. The record or data which is stored within the device for diabetes management is capable of being downloaded to a remote site for access and review by a health care professional or physician. Additionally, other records are capable of being received by the device for diabetes management from a remote site for use by the diabetic patient. Moreover, the device for diabetes management of the present invention enables an individual to factor in other variables besides carbohydrate food content such as other factors being exercise and existing glucose levels which also impact glucose control. Additional other factors are, for example, variation of insulin sensitivity during the course of the day or the different effect on blood glucose levels by different foods of the same food category of equivalent caloric value. Foods from the same food group may nevertheless alter glucose levels in a differing manner can be said to have different glycemic indexes. The use of the glycemic index control on the device allows this variant to be considered when calculating carbohydrate intake or insulin requirements. The device of the present invention allows for more accurately determining the dosage of insulin for a diabetic.

SUMMARY OF THE INVENTION

The present invention is a device for management of diabetes which comprises a programmable microprocessor based unit having a display, keyboard, and memory means, means for inputting information concerning carbohydrates ingested by a user, means for determining an amount of insulin to be used by a user based upon the carbohydrates ingested, means for displaying the amount of insulin to be used in the display of the unit.

In another form, the present invention is a device for management of diabetes comprising a microprocessor having memory means, a keyboard operatively connected to the microprocessor for entering information concerning an amount of carbohydrates ingested by a user, the microprocessor having stored in the memory means a program for determining an amount of insulin to be administered by a user based upon the amount of carbohydrates ingested, and a display operatively connected to the microprocessor for displaying the amount of insulin determined by the program stored in the memory means.

In still another form, the present invention is a device for management of diabetes comprising: a programmable microprocessor based unit having a display, keyboard, and memory means, the keyboard comprising a plurality of keys with a portion of the keys arranged in a matrix such that a row of keys is representative of a food group and a column of keys is representative of increasing amounts of carbohydrates within the food group, means for inputting information corresponding to an amount of carbohydrates ingested by a user means for determining an amount of insulin to be used by a user based upon the amount of carbohydrates ingested and means for displaying the amount of insulin to be used.

In light of the foregoing comments, it will be recognized that a principal object of the present invention is to provide an improved device for diabetes management.

A further object of the present invention is to provide a device for diabetes management which is of simple construction and design and which can be easily employed with highly reliable results.

Another object of the present invention is to provide a device for diabetes management which is a hand-held unit and is easy to operate.

A further object of the present invention is to provide a device for diabetes management which allows recording of the amount of carbohydrates consumed by a patient to better manage a patient's diet.

These and other objects and advantages of the present invention will become apparent after considering the following detailed specification in conjunction with the accompanying drawings, wherein:

DETAILED DESCRIPTION OF THE PREFERRED EMBODIMENTS

Figure 1:
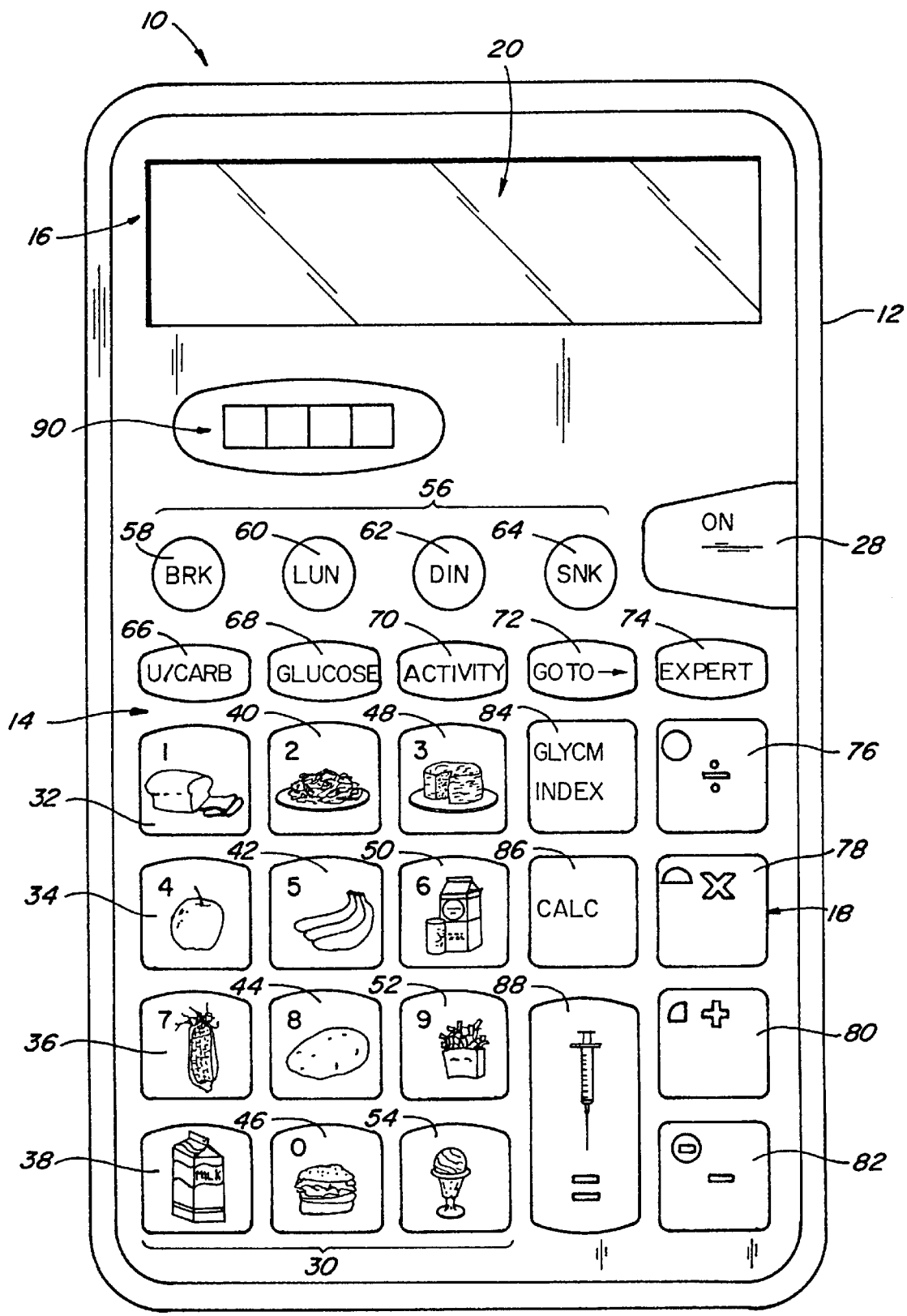
FIG. 1 is a perspective view of a device for management of diabetes constructed according to the present invention.

Referring now to the drawings, wherein like numbers refer to like items, number 10 identifies a preferred embodiment of a device for management of diabetes constructed according to the present invention. The device 10 is shown in FIG. 1 to comprise a hand-held unit 12 having a keyboard 14 and a display 16. The keyboard 14 includes a plurality of keys 18 which are adapted to be actuated by a user of the device 10. The function and control of each of the keys 18 will be discussed in detail later. The display 16 includes two rows of elements 20 such as LCD elements which are capable of displaying alpha-numeric information. The unit 12 is similar to a hand-held calculator device.

Figure 2:
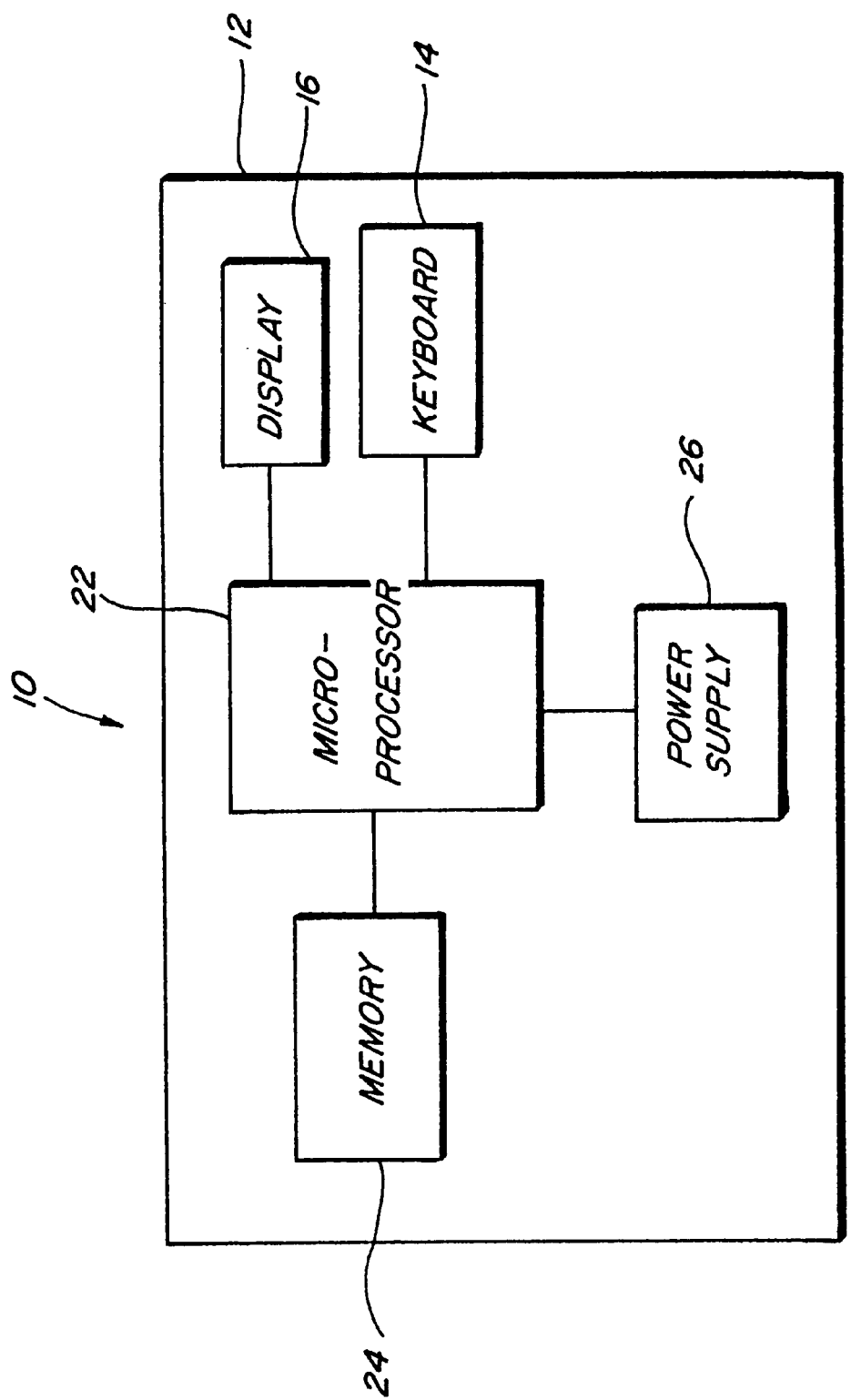
FIG. 2 is a block diagram of the device for management of diabetes.

With reference now to FIG. 2, the device 10 is shown to comprise the housing 12, the keyboard 14, the display 16, and the interior of the housing 12 includes a microprocessor 22 that interfaces with the keyboard 14 and the display 16. The microprocessor 22 is also connected to a memory circuit 24 and a power supply 26. The memory circuit 24 can include both ROM and RAM type memory circuits and the memory circuit 24 can be either internal or external to the microprocessor 22 as may also be removable from the device 10, as is well known. The device 10 may include other circuitry such as an RS-232 port, infra red link, or a modem, all of which are not shown, for transmitting and/or receiving information. For example, with use of such known data ports it is possible to transfer data from the device 10 to a personal computer to analyze data stored in the device 10. Additionally, the device 10 may be capable of receiving data via the port for downloading information as required. The device 10 is also capable of having information initialized within the memory circuit 24 to reflect particular attributes for the particular patient and therefore have standard calculations modified for the particular patient. The device 10 also includes circuitry (not shown) associated with the microprocessor 22 for determining whether the device 10 has been powered for a predetermined time period without any of the keys 18 being depressed. If the device 10 determines that the predetermined time period has elapsed without any of the keys 18 being actuated the device 10 will turn itself off.

The function of each of the keys 18 will now be described in detail with reference being made again to FIG. 1. The device 10 is powered by pressing an ON key 28. A group 30 of the keys 18 have pictorial representations of foods which have carbohydrates associated with each of the keys 18. Within the group 30 is a key 32 which is indicative of a slice of bread being eaten, a key 34 is indicative of an apple being eaten, a key 36 is illustrated to be representative of corn being eaten, and a key 38 represents a serving of milk. Continuing to the next column of keys 18 within the group 30 there is a key 40 which is associated with a serving of pasta, a key 42 is indicative of a serving of a banana, a key 44 represents a potato being eaten, and a key 46 indicates a serving of a hamburger. The last column within the group 30 has a key 48 which represents a piece of cake being eaten, a key 50 indicates a serving of orange juice, a key 52 which is used to show that a serving of french fries has been consumed, and a key 54 which represents a serving of ice cream. The keys 32–36 and 40–54 also serve a dual function as being numeric keys for a calculator. For example, key 32 represents the numeral one, key 40 represents the numeral two, key 48 represents the numeral three, key 34 represents the numeral four, key 42 represents the numeral five, key 50 represents the numeral six, key 36 represents the numeral seven, key 44 represents the numeral eight, key 52 represents the numeral nine, key 46 represents the numeral zero, and key 54 represents the decimal point.

The keyboard 14 further includes a group 56 of keys 18 which has a type of meal associated with each of the keys 18. In the group 56 a key 58 is indicative of breakfast, a key 60 represents lunch, a key 62 indicates dinner, and a key 64 is representative of a snack being eaten by a user. Additionally, the keys 58, 60, 62, and 64 in the group 56 are appropriately abbreviated, for example, key 58 has the abbreviation BRK for breakfast, key 60 has LUN for lunch, key 62 has DIN for dinner, and key 64 has SNK for snack. A key 66 has the abbreviation U/CARB which is used to indicate that the user of the device 10 is on insulin and will require the device 10 to determine a dosage of insulin to be used by the user. A key 68 is labeled GLUCOSE and is used to enter a glucose level of the user. An ACTIVITY key 70 is used to enter information concerning whether the user has had any exercise. A GOTO key 72 is used to bypass an instruction, as will be explained. A key 74 is labeled EXPERT and allows the user to enter an expert mode of operation of the device 10, as will be explained. Additionally, by entering the expert mode the user may bypass certain instructions or prompts from the device 10.

In order to indicate the size or portion of food eaten, keys 76, 78, 80, and 82 are provided on the keyboard 14. The key 76 represents a large portion of food being eaten and has a full circle imprinted on the key 76. The key 78 is used to represent a medium portion of food being eaten which is represented by a half circle on the key 78. A small portion is shown on the key 80 which is represented by a quarter circle being printed on the key 80. Key 82 is used to reduce a portion amount and has displayed thereon a full circle with a minus sign. The keys 76, 78, 80, and 82 also serve the dual purpose of arithmetic functions such as key 76 representing the division operation, key 78 representing the multiplication function, key 80 representing the addition function, and key 82 representing the substraction operation.

A key 84 is identified as the GLYCM INDEX which allows the user to enter a glycemic index value into the device 10. As stated above, foods from the same food group may alter glucose levels in a differing manner and have different glycemic indexes. Entering information concerning a glycemic index has an impact on the calculation of the amount of insulin required based upon carbohydrate intake.

A key 86 which is titled CALC is used to switch the device 10 between operation as a calculator and the diabetes management device of the present invention. The keyboard 14 has a key 88 which, when pressed, will allow the device 10 to determine an insulin dosage based upon certain previously entered information. The key 88 has a syringe illustrated thereon to represent this function. Additionally, when the device 10 is in the calculator mode, the key 88 functions as the equal sign key of a calculator. A solar cell 90 may also be provided to power the device 10 and the solar cell 90 is part of the power supply 26.

Figure 3:
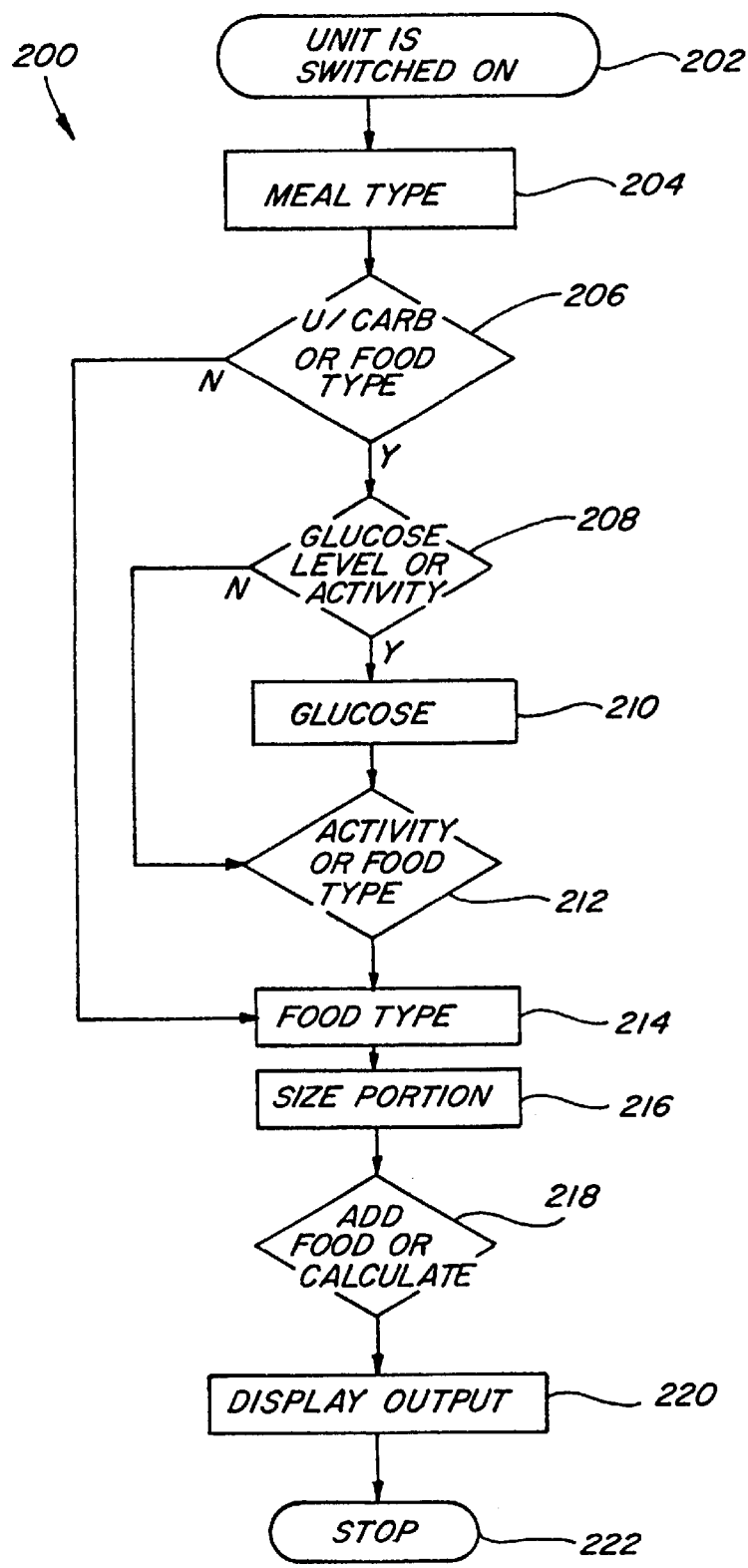
FIG. 3 is a flow chart illustrating one process of operation of the device.

The use of device 10 is best illustrated by reference to FIG. 3 wherein a flow chart of a program 200 is shown which controls the device 10. The program 200 may be stored in the memory circuit 24 of the microprocessor 22. Operation of the program 200 begins at a step 202 in which the device 10 is turned on by pressing the key 28, the ON key. Control of the program 200 then passes to a step 204 in which the user is prompted by a message in the display 16 to enter a meal type. Entry of a meal type is accomplished by pressing one of the meal type keys 58, 60, 62, or 64. For example, if the user has eaten breakfast, then the breakfast key 58 will be selected. Once one of the meal type keys 58-64 has been pressed this information is stored in the microprocessor 22 and the program continues on to a step 206. In step 206 the user is queried by the display 16 as to whether the user is on insulin. If the user is on insulin the U/CARB key 66 is pressed and the display 16 changes to read the number of units associated with the meal type entered in step 204. For example, the display 16 may read 1.0 u/15 g. The 15 g is a standard setting by default with such default setting being able to be changed as will be explained. If in step 206 the user is not on insulin the user will press the GOTO key 72 and control of the program 200 branches to a step 214. If, however, in step 206 the user has pressed the U/CARB key 66 then the program 200 continues to a step 208. Step 208 requests the user to either enter the user's glucose level or press the GOTO key 72 which indicates that the user wants to bypass this step 208 and the program 200 would then branch to a step 212. If the user elects to enter the glucose level then the user enters the numeric number for the glucose level by pressing the required numeral keys 32-36 and 40-52. For example, if the glucose level of the user has been measured to be 170 the user would press keys 32, 36, and 46. The display 16 would also show the number entered by the user. Once the glucose level number has been entered and displayed control of the program 200 passes to a step 210. In step 210 the display 16 reads IF CORRECT PRESS GLUCOSE and the user is required to press the GLUCOSE key 68 to confirm that the correct glucose level number has been entered. The device 10 is also programmed to determine if a proper glucose level number has been entered by the user. For example, if the glucose level number is less than 60 the display 16 will show ALERT which indicates to the user that an improper number has been entered. Once the GLUCOSE key 68 has been pressed the program passes to step 212. Step 212 attempts to determine if the user has exercised. In this situation the display 16 reads IF EXERCISE USE ACTIVE OR GOTO which requires the user to either press the ACTIVITY key 70 or the GOTO key 72. If the GOTO key 72 is selected the program 200 will continue on to step 214. If, however, the user presses the ACTIVITY key 70 then the program 200 stores the fact that the ACTIVITY key 70 has been pressed and the program 200 passes to step 214.

Step 214 prompts the user to press one of the food keys 32-54 to enter the food type the user has eaten. For example, if the user has eaten a banana then the key 42 would be selected. If for some reason the user pressed the wrong food key 32-54, selection of key 82 would have to be pressed. Once the food type has been entered the program 200 moves on to a step 216. In step 216 the user is requested to enter the portion size of the food type entered in step 214. This is accomplished by pressing one of the keys 76, 78, or 80. More particularly, selection of the key 76 indicates that a large portion of food was eaten, selection of the key 78 represents a medium portion of food was eaten, and selection of the key 80 indicates that a small portion of food was eaten. After the size information has been entered, control of the program 200 passes to a step 218. In step 218 the user is prompted to determine if additional food has been eaten and if so the user will press one of the food type keys 32-54. Upon the entering of one of the food type keys 32-54 the program 200 will loop back to step 214. If the user has finished the entering of food eaten the user presses the syringe key 88 and the program passes to a step 220. In step 220 the device 10 calculates the insulin dosage required to be used by the user. However, if in step 206 the user indicated that the user was not taking insulin the device 10 will now calculate and display food data which consists of the total for the entry, the total for the day, and the recommended daily allowance. Once either the insulin dosage amount or the food data is displayed the program 200 will stop at a step 222.

Some representative default values for the device 10 will now be described. The food keys 32-54 will have a certain number of grams associated with the particular food type and the particular portion size. The keys 32, 34, 36, and 38 will all have the following grams (g) associated with each of the keys 32-38: small portion 10 g, medium portion 15 g, and large portion 20 g. The keys 40, 42, 44, and 46 will have the following grams associated with each of the keys 40-48: small portion 20 g, medium portion 30 g, and large portion 40 g. The key 48 has default values of 30 g for a small portion, 45 g for a medium portion, and 60 g for a large portion. The key 50 has default values of 20 g for a small portion, 30 g for a medium portion, and 45 g for a large portion. The key 52 has default values of 35 g for a small portion, 45 g for a medium portion, and 50 g for a large portion. The key 54 has default values of 20 g for a small portion, 30 g for a medium portion, and 40 g for a large portion.

With respect to the glucose level number entered by the user the following are default values which are used by the device 10. If the user enters a glucose level below 151 then there is no change on the insulin dosage. A glucose level between 151 and 200 would add 0.5 units of insulin to the calculated dosage. If the user enters a glucose level number between 201 and 250 one unit would be added to the calculated insulin dosage. A glucose level number between 251 and 300 would add 1.5 units to the insulin dosage number. If an entered glucose level is between 301 and 350 then 2 units would be added to the insulin dosage. If the user enters a glucose level number between 351 and 400 then 2.5 units are added to the insulin dosage. Additionally, if the ACTIVITY key 70 is pressed two insulin units would be subtracted from the insulin dosage number.

Additional steps may be included in the program 200. For example, an additional step may be added between steps 216 and 218 wherein the user is able to enter the glycemic index value. The user will be capable of entering a value for the glycemic index which will have an impact on the calculation of insulin to be taken. The glycemic index is entered by pressing the key 84.

The expert mode of operation of the device 10 may be entered by pressing the key 74. Once the key 74 is pressed the user enters information without having any of the prompts appear in the display 20. The control of the program 200 would be similar except for no prompts would be displayed and considerable time would be saved by the user. The user of the device 10 would be able to use the expert mode after obtaining some experience with the device 10.

From all that has been said, it will be clear that there has thus been shown and described herein a device for management of diabetes which fulfills the various objects and advantages sought therefor. It will be apparent to those skilled in the art, however, that many changes, modifications, variations, and other uses and applications of the subject device for management of diabetes are possible and contemplated. All changes, modifications, variations, and other uses and applications which do not depart from the spirit and scope of the invention are deemed to be covered by the invention, which is limited only by the claims which follow.

What is claimed is:

1. A device for management of diabetes comprising:

a microprocessor having storage means;

a keyboard operatively connected to the microprocessor for entering information representative of a food ingested by a user, the keyboard having a plurality of keys with a portion of the keys representative of a food group and each of the keys corresponding to an amount of carbohydrates within the food ingested by a user;

the microprocessor having stored in the storage means a program for determining an amount of insulin to be administered by a user based upon the corresponding amount of carbohydrates within the food ingested; and a display operatively connected to the microprocessor for displaying the amount of insulin determined by the program stored in the storage means.

2. The device of claim 1 wherein the keyboard further comprises means for entering a meal type ingested by a user.

3. The device of claim 1 wherein the keyboard further comprises means for entering a glucose level of a user.

4. The device of claim 1 wherein the keyboard further comprises means for entering an activity status of a user.

5. The device of claim 1 wherein the keyboard further comprises means for entering a portion size of the food ingested by a user.

6. The device of claim 1 wherein the keyboard further comprises means for entering a glycemic index of a food ingested by a user.

7. A device for management of diabetes comprising:

a microprocessor having storage means;

a keyboard operatively connected to the microprocessor for entering information representative of a food ingested by a user, the keyboard having a plurality of keys with a portion of the keys representative of a food group and each of the keys corresponding to an amount of carbohydrates within the food ingested by a user and another portion of the keys for entering a glycemic index of a food ingested by a user;

the microprocessor having stored in the storage means a program for determining an amount of insulin to be administered by a user based upon the amount of carbohydrates ingested and the glycemic index entered; and a display operatively connected to the microprocessor for displaying the amount of insulin determined by the program stored in the storage means.

8. The device of claim 7 wherein the keyboard further comprises means for entering a meal type ingested by a user.

9. The device of claim 7 wherein the keyboard further comprises means for entering a glucose level of a user.

10. The device of claim 7 wherein the keyboard further comprises means for entering an activity status of a user.

11. The device of claim 7 wherein the keyboard further comprises means for entering a portion size of the food ingested by a user.

12. A device for management of diabetes comprising:

a programmable microprocessor based unit having a display, keyboard, and storage means, the keyboard comprising a plurality of keys with a portion of the keys arranged in a matrix such that a row of keys is representative of a food group and a column of keys is representative of increasing amounts of carbohydrates within the food group;

means for inputting information representative of an amount of carbohydrates ingested by a user;

means for inputting a glycemic index of a food ingested by a user;

means for determining an amount of insulin to be used by a user based upon the representative amount of carbohydrates ingested and the glycemic index; and means for displaying the amount of insulin to be used.

13. The device of claim 12 wherein the keyboard further comprises means for entering a meal type ingested by a user.

14. The device of claim 12 wherein the keyboard further comprises means for entering a glucose level of a user.

15. The device of claim 12 wherein the keyboard further comprises means for entering an activity status of a user.

16. The device of claim 12 wherein the keyboard further comprises means for entering a portion size of the food ingested by a user.

* * * * *